United States Patent
Folchini

[11] Patent Number: 6,164,472
[45] Date of Patent: Dec. 26, 2000

[54] METAL BOTTLE CAP

[75] Inventor: Enrico Folchini, S. Maria Maddalena, Italy

[73] Assignee: Pelliconi Abruzzo S.r.l., Italy

[21] Appl. No.: 09/368,060

[22] Filed: Aug. 3, 1999

Related U.S. Application Data

[63] Continuation-in-part of application No. 08/999,855, Dec. 29, 1997, abandoned, which is a continuation-in-part of application No. 08/799,801, Feb. 13, 1997, abandoned, which is a continuation-in-part of application No. 08/527,183, Sep. 12, 1995, abandoned.

[30] Foreign Application Priority Data

Sep. 23, 1994 [IT] Italy ................... B094A0416

[51] Int. Cl.$^7$ ................................. B65D 41/10
[52] U.S. Cl. ............................................ 215/328
[58] Field of Search ..................... 215/324–328, 215/318, 317, 329

[56] References Cited

U.S. PATENT DOCUMENTS

| | | | |
|---|---|---|---|
| 3,648,874 | 3/1972 | Moller | 215/328 |
| 3,774,795 | 11/1973 | Leenaards | 215/328 |
| 5,458,253 | 10/1995 | Shapcott | 215/328 |

FOREIGN PATENT DOCUMENTS

| | | | |
|---|---|---|---|
| 3906112 | 8/1990 | Germany | 215/328 |

*Primary Examiner*—Nathan J. Newhouse
*Attorney, Agent, or Firm*—Orum & Roth

[57] ABSTRACT

A metal bottle cap consisting of a central body to close off an opening at the neck of the bottle and an outer crown which is integral with the central body and is made up of a uninterrupted plurality of teeth which may be bent and fixed around the rim over a thread which has a number of starts on a bottleneck, the number of teeth on the outer crown must be different to a whole multiple of the number of starts on the rim of the bottle; and should be between twenty-nine and thirty-three.

7 Claims, 3 Drawing Sheets

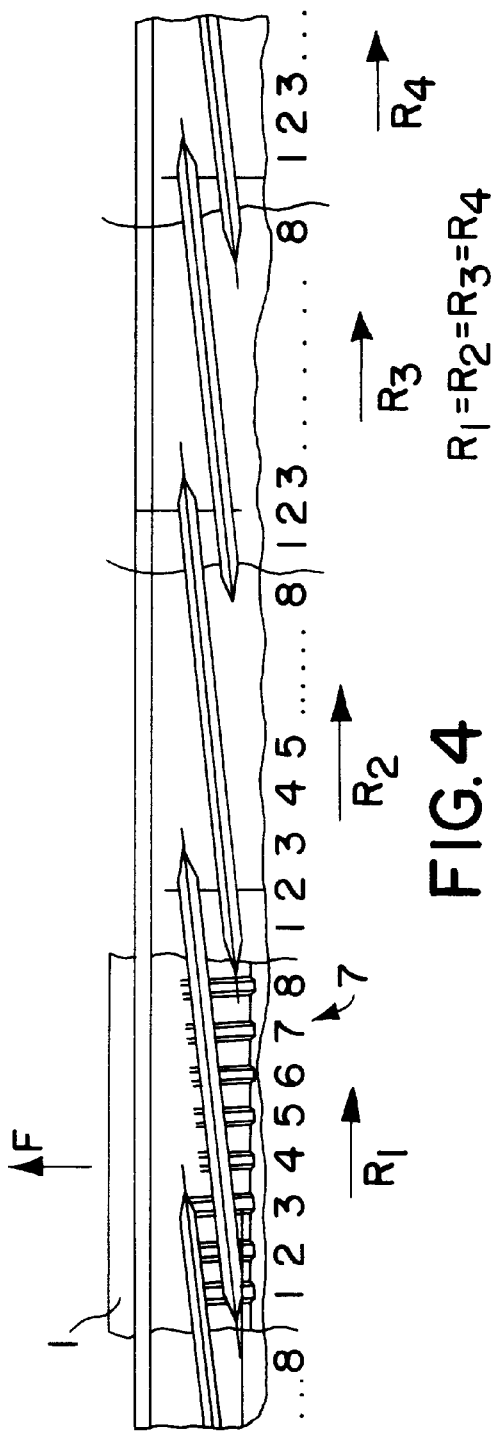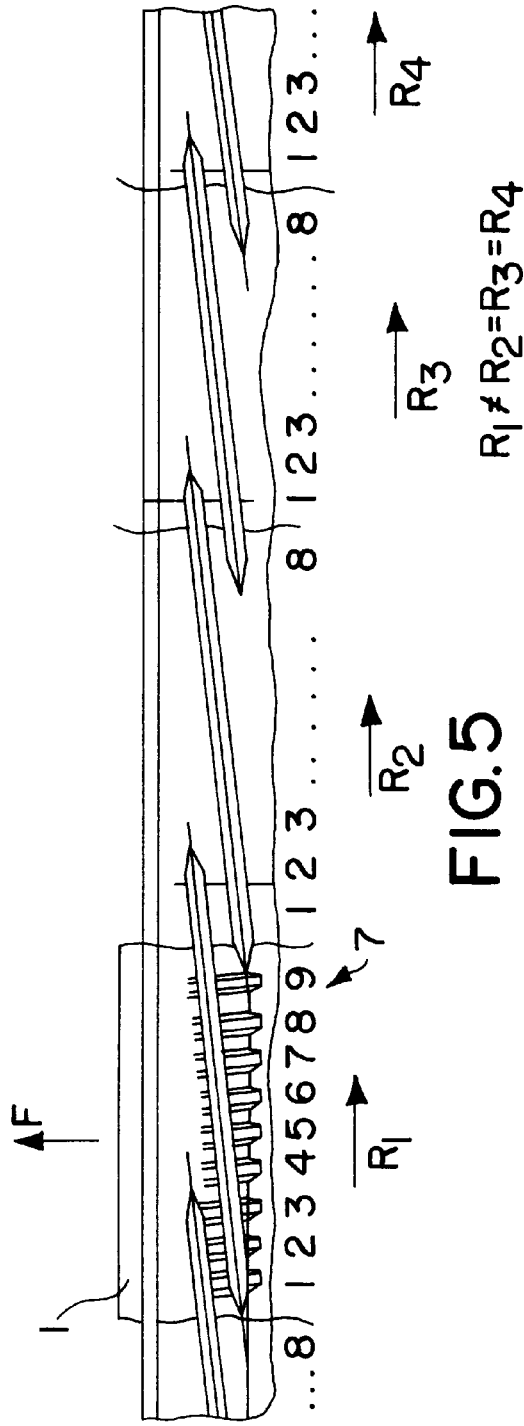

METAL BOTTLE CAP

This is a Continuation-In-Part of Application U. S. Ser. No. 08/999,855, filed on Dec. 29, 1997, now abandoned which was a Continuation-In-Part of Ser. No. 08/799,801, which was filed on Feb. 13, 1997, now abandoned which was a Continuation-In-Part of Ser. No. 08/527,183, filed on Sep. 12, 1997.

BACKGROUND of the INVENTION

The present invention relates to a metal cap which hermetically seals bottles, and is particularly aimed at glass bottles containing liquid foodstuffs under pressure.

This crown-cap is already well known and has been used for some time by bottling companies to seal many types of glass bottles, above all for drinks bottled under pressure, such as beer, Coca-Cola, lemonade, etc.

The circular central body of the cap has a suitable pressure-tight lining (usually made of synthetic, thermoplastic material for example PVC, polyethylene derivatives, or natural material such as cork) on the internal surface which is placed against a bottle neck opening. the outer crown is made up of corrugations which may be bent down to form a plurality of teeth which hold the cap firmly on to the rim of the bottleneck.

It is also well known that you need a bottle-opener always in hand to open a bottle sealed with the classical crown-cap.

This particular "problem" with opening has led some drinks manufacturers to produce a so-called "hybrid" solution: by closing the bottle with a screw-off crown cap. In practice this particular type of cap (in commercial jargon called "twist off") is made up of a normal crown-cap with twenty one teeth which is firmly placed around the rim of the bottle, which is obviously fitted with the necessary thread for unscrewing the cap. So the twist off cap has basically the same structure as the crown-cap but the teeth are fixed over the external thread which protrudes from the bottleneck.

The main problem with this solution is that it is not very comfortable to open by hand. The cap must be fix very firmly to the bottle to maintain the pressure of the liquid inside the bottle and to avoid the risk of leakage during normal handling. So a certain amount of force which not everyone may have, is needed to rotate the cap in order to open the bottle. this operation also carries the risk of injuring or cutting the hands due to the "sharp edges" of the teeth on the crown.

With this in mind several devices have been proposed to enable users to "twist off" the bottle cap swiftly (see also Canadian patent N. 1.252.431), but these are obviously considered accessories and must be on hand for the user to unscrew the cap.

SUMMARY OF THE INVENTION

The stated object is comprehensively realized in the bottle cap disclosed, wherein a metal "twist off" cap to seal glass bottles which can be comfortably and safely unscrewed by hand with out altering the standards of safety and stability of the pressurized seal of the outer cap. This result is accomplished by choosing the number of teeth on the outer cap crown to be different to a whole number multiple of the number of thread starts or ends on the rim of the bottle.

BRIEF DESCRIPTION OF THE DRAWINGS

This invention will now be described in detail, by way of example, with the aid of the accompany drawing, in which:

FIG. 4 is a partial side view showing a bottle neck with four thread starts, and a partial cap having a total of 32 teeth;

FIG. 5 is a partial bottle neck side view of FIG. 4 with a partial cap having 33 teeth;

DETAILED DESCRIPTION OF THE PREFERRED EMBODIMENT

Figure 1:
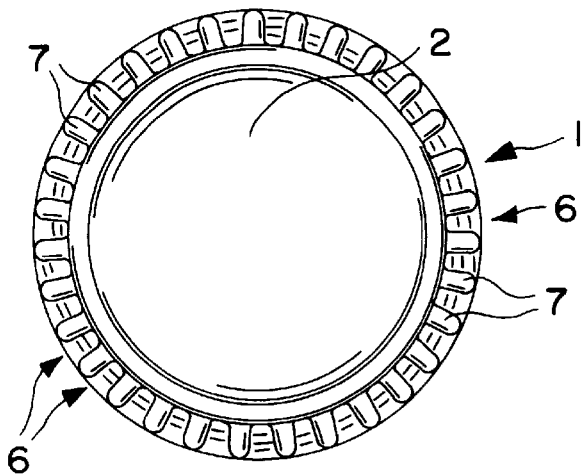
FIG. 1 is a plan-view of the bottle cap of the present invention.
Figure 2:
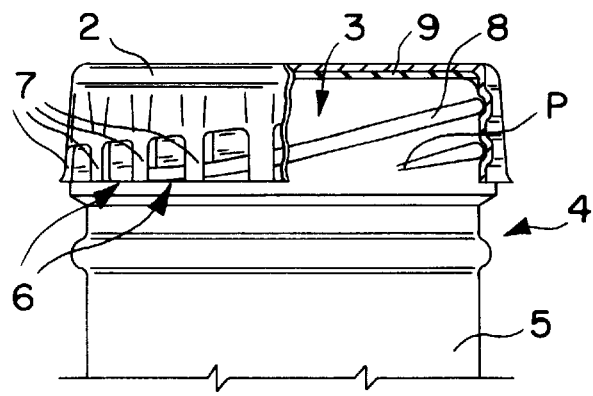
FIG. 2 is an enlarged front view partially in cross-section of the cap in FIG. 1 applied to a bottleneck.

With reference to the accompanying drawings, the invention relates to a metal bottle cap (denoted 1) is the type of bottle top known as "twist off" and is used for bottles containing liquid foodstuffs.

The cap (1) consists of the central body (2) which covers the opening (3) of the rim (4) of the bottle (5) and the outer crown (6) which is integral with the central body (2). The central body (2) also has a lining (9) on the internal side which faces the bottle opening (5) and enhances closing of the bottle.

The outer crown (6) is an uninterrupted plurality of teeth (7) which may be bent and fixed onto the rim (4) over a thread (8) on the rim; the number (P) of starts of this thread (8) is variable and depends on the type of bottle to be closed. In this case the number four has been chosen purely as an example (it is the most frequently used); in this way the cap (1) is firmly fixed to the rim (4), or rather with the teeth (7) closed gripping the thread (8) a perfect seal is obtained, but at the same time it is possible to open the bottle simply by unscrewing the cap (1) by hand.

The traditional number of teeth (7) for the crown-cap is twenty one. The Applicant has discovered that raising this number facilitates opening and reduces the possible risk of cuts or injury to the user's hand when rotating the cap (1).

It has been found that the unstableness of the cap or the bottle is particularly evident with the cap having a number of teeth that is a multiple of the number of starts of the thread on the rim of the bottle.

Considering that, normally, the number of starts of the thread on the rim of the bottle is three or four, and preferably four (because with four starts the bottle can be opened with a rotation of about 90 degrees of the cap), the number of teeth that are "prohibited" are all the multiples of three and four. Considering that the preferred range of the number of teeth in the twist-off caps is compromised between 28 and 32, because of a comfortable and safe grip of the cap by the hand, the combinations to be excluded are 30 teeth if the rim of the bottles has three starts and 28 and 32 teeth if the rim of the bottle has four starts.

From a practical aspect, the bottles with three starts in the thread of the rim of the bottle is of no interest because of the greater angle (almost 120 degrees) necessary for the unscrewing action of the cap. Nevertheless, if the rim of the Bothell's three starts, the solution with 33 teeth must be excluded.

In other words, the possible combinations of starts versus teeth are 28, 29, 31, 32 teeth if the rim of the bottle has three starts and 29, 31, 33 teeth if the rim of the bottle has four starts. Therefore, it is preferable to limit the numbers of teeth for the cap of 29, 31, and 33 in combination with the four starts four the thread in the rim of the bottle. These numbers of the teeth appear to be also suitable for a hypothetical new bottle with five starts for the thread in the rim of the bottle.

The reasons for this propensity of a cap to unscrew itself from the bottle when the cap has a number of teeth multiple of number of starts in the rim of the bottle can best be understood as follows.

Considering the rectified rim of the bottle, as shown in FIG. 4, it can be seen that, in the case of four starts for the thread and 32 teeth for the cap, on each thread are crimped 8 teeth. The resulting rotation forces R1, R2, R3, R4, that are transferred from the cap to the threads by means of the teeth, are equal and axially symmetrically disposed. Furthermore, for a pressure within the bottle, the opening pressure is determined by dividing the number of teeth (8), into the pressure.

On the contrary, with 33 teeth, as shown in FIG. 5, the number teeth per thread are not equal and the rotation forces are not equally distributed on the four threads (e.g. r1 is different from the other resulting rotation forces). Consequently the rotation forces are not axially symmetrically disposed, leaving at least one start with higher sealing pressure, which is calculated by dividing the number of teeth (7) into the same pressure. The conclusion is that the equality and the symmetry of the rotation forces, when the number of teeth corresponds to a multiple of the number of starts, facilitates the selfrotation of the cap and thus the unscrewing of the cap.

As mentioned, many possible alternatives were studied to find the number of teeth (7) which permits comfortable and safe manual opening of a cap (1) which is held firmly onto the bottle. Eventually a correlation was found between the number of teeth (7) and the number of starts (P) of the thread (8) on the rim (4) of the bottle (5). In fact it was ascertained that the cap (1) became less stable over time if the number of teeth (7) was equal and corresponded to a multiple of the number of starts (P) of the thread (8).

Figure 3:
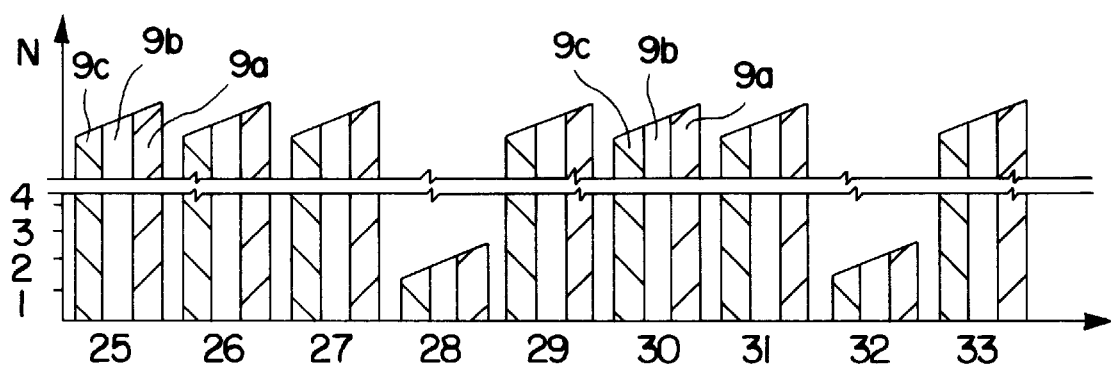
FIG. 3 is a graph where the number of weeks the cap maintained the seal are plotted against the number of teeth on the cap.

This correlation is clearly visible on the graph in FIG. 3. where several caps with different numbers of teeth (7) (from twenty-five to thirty-three to be exact, which is clearly labeled on the graph) and relative linings (9) made of different material (that is with high 9a, medium 9b and low 9c grip) are on the horizontal axis. The number of weeks the cap (1) maintained a correct and stable hold on the bottle (5) is plotted on the vertical axis. As can be seen from the graph in FIG. 3 the caps with twenty-eight and thirty-two teeth have a short seal life, irrespective of the material used for the lining (9). while the caps (1) with a number of teeth (7) which is not a multiple of the number starts (P) of the thread (8) maintain their hold for a considerable number of weeks.

In particular the optimal "range" for the number of teeth (7) on the outer crown (6) proved to be twenty-nine, thirty-one or thirty-three. If the rim (4) of the bottle (5) has four starts (P) of the thread (8) the best solution is for the cap (1) to have thirty-one teeth or thirty-three (7) (which is in fact a prime number and not a whole number to the number of thread starts).

Figure 6:
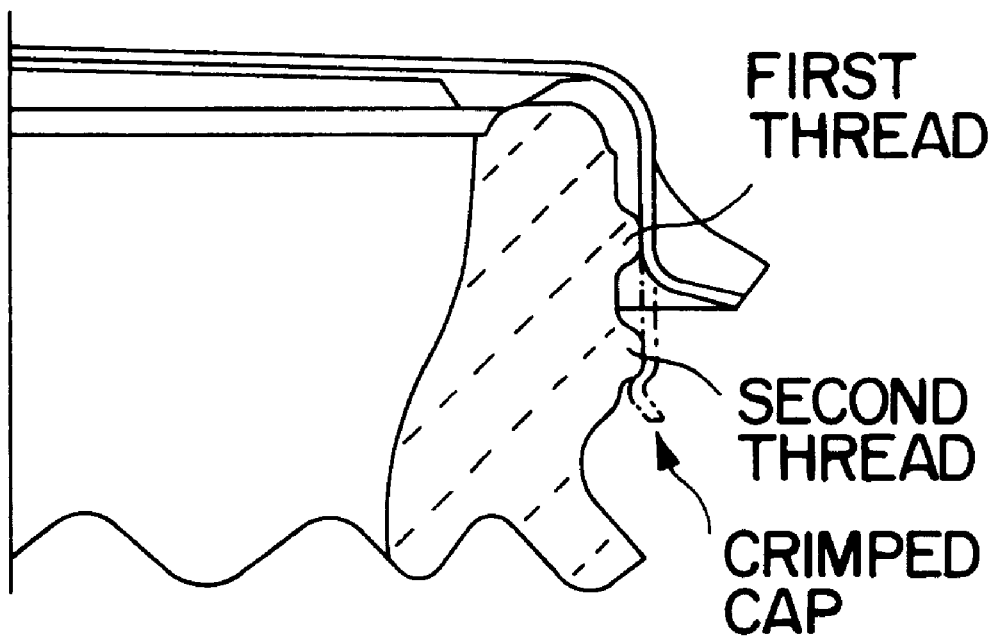
FIG. 6 is a partial cross sectional view of a prior art cap emphasizing a probable cap leak site between a thread start and a thread end finish between overlapping bottle threads.

Referring to FIG. 6, it is seen from the prior art arrangement that in the situation where a top thread of a first thread start and bottom thread of a second and overlapping thread start, a problem is caused due to a division of the crimping forces between the thread starts. In that instance when one thread begins and the other ends, at least one tooth is in a situation where the crimping of the cap tooth on the second thread is more difficult and not as strong as against the top thread, thereby creating a propensity of the cap to unseat and leak in this area.

With this invention the objects have been achieved in that the greater number of teeth makes fast and safe opening possible by rotation of the cap around the rim while ensuring the bottle is sealed as securely as bottles sealed with the traditional crown-cap system.

During the experiments it was found that the above mentioned ideal number of teeth is thirty-one, which is also perfectly suitable for bottles with threads with three starts, as thirty-one is a prime number; it is not divisible by three.

The invention described can be subject to modifications and variations without thereby departing from the scope of the inventive concept. Moreover, all details of the invention may be substituted by technical equivalent elements.

What is claimed is:

1. A steel twist-off bottle cap in a combination with a bottle, said bottle containing a pressurized drink content and including a neck which has an opening therein for dispensing said drink contents from within said bottle, said opening in said neck defining a rim that has four thread starts thereon, each of said thread starts having a respective start end and a finish end, said cap having a central body for closing off the opening at the neck of the bottle and an outer crown integral with the central body, said outer crown comprising thirty-three uninterrupted teeth bent around and fixed onto the rim, wherein the number of teeth crimped on each of the thread starts is different for at least one of the thread starts with respect to the other three thread starts, whereby the number of teeth is different to a whole multiple of the number of thread starts such that at most only one tooth of said cap is ever located at and aligned with one of said thread start and finish ends, thereby reducing a tendency of the cap to unscrew itself and a propensity for said contents to leak from said bottle before said cap is removed therefrom.

2. A steel twist-off bottle cap in a combination with a bottle, said bottle containing a pressurized drink content therein and including a neck which has an opening therein for dispensing said drink contents from within said bottle, said opening in said neck defining a rim that has four thread starts thereon, each of said thread starts having a respective start end and a finish end, said cap having a central body for closing off the opening at the neck of the bottle and an outer crown integral with the central body, said outer crown comprising an uninterrupted twenty-nine teeth bent around and fixed onto the rim, wherein the number of teeth crimped on each of the thread starts is different for at least one of the thread starts with respect to the other three thread starts, whereby the number of teeth is different to a whole multiple of the number of thread starts such that at most only one tooth of said cap is ever located at and aligned with one of said thread start and finish ends, thereby reducing a tendency of the cap to unscrew itself and a propensity for said contents to leak from said bottle before said cap is removed therefrom.

3. A steel twist-off bottle cap in a combination with a bottle, containing a pressurized drink contents and including a neck which has an opening therein for dispensing said drink contents from within said bottle, said opening in said neck defining a rim that has four thread starts thereon, each of said thread starts having a respective start end and a finish end, said cap having a central body for closing off the opening at the neck of the bottle and an outer crown integral with the central body, said outer crown comprising an uninterrupted 31 teeth bent around and fixed onto the rim, wherein the number of teeth crimped on each of the thread starts is different for at least one of the thread starts with respect to the other three thread starts, thereby reducing the tendency of the cap to unscrew itself, whereby the number of teeth is different to a whole multiple of the number of thread starts such that at most only one tooth of said cap is ever located at and aligned with one of said thread start and finish ends, thereby reducing a propensity for said contents to leak from said bottle before said cap is removed therefrom.

4. A steel twist-off bottle cap in a combination with a bottle, containing a pressurized drink contents and including a neck which has an opening therein for dispensing said drink contents from within said bottle, said opening in said neck defining a rim that has three thread starts thereon, each of said thread starts having a respective start end and a finish end, said cap having a central body for closing off the opening at the neck of the bottle and an outer crown integral with the central body, said outer crown comprising an uninterrupted 28 teeth bent around and fixed onto the rim, wherein the number of teeth crimped on each of the thread starts is different for at least one of the thread starts with respect to the other two thread starts, thereby reducing the tendency of the cap to unscrew itself, whereby the number of teeth is different to a whole multiple of the number of thread starts such that at most only one tooth of said cap is ever located at and aligned with one of said thread start and finish ends, thereby reducing a propensity for said contents to leak from said bottle before said cap is removed therefrom.

5. A steel twist-off bottle cap in a combination with a bottle, containing a pressurized drink contents and including a neck which has an opening therein for dispensing said drink contents from within said bottle, said opening in said neck defining a rim that has three thread starts thereon, each of said thread starts having a respective start end and a finish end, said cap having a central body for closing off the opening at the neck of the bottle and an outer crown integral with the central body, said outer crown comprising an uninterrupted 29 teeth bent around and fixed onto the rim, wherein the number of teeth crimped on each of the thread starts is different for at least one of the thread starts with respect to the other two thread starts, thereby reducing the tendency of the cap to unscrew itself, whereby the number of teeth is different to a whole multiple of the number of thread starts such that at most only one tooth of said cap is ever located at and aligned with one of said thread start and finish ends, thereby reducing a propensity for said contents to leak from said bottle before said cap is removed therefrom.

6. A steel twist-off bottle cap in a combination with a bottle, containing a pressurized drink contents and including a neck which has an opening therein for dispensing said drink contents from within said bottle, said opening in said neck defining a rim that has three thread starts thereon, each of said thread starts having a respective start end and a finish end, said cap having a central body for closing off the opening at the neck of the bottle and an outer crown integral with the central body, said outer crown comprising an uninterrupted 31 teeth bent around and fixed onto the rim, wherein the number of teeth crimped on each of the thread starts is different for at least one of the thread starts with respect to the other two thread starts, thereby reducing the tendency of the cap to unscrew itself, whereby the number of teeth is different to a whole multiple of the number of thread starts such that at most only one tooth of said cap is ever located at and aligned with one of said thread start and finish ends, thereby reducing a propensity for said contents to leak from said bottle before said cap is removed therefrom.

7. A steel twist-off bottle cap in a combination with a bottle, containing a pressurized drink contents and including a neck which has an opening therein for dispensing said drink contents from within said bottle, said opening in said neck defining a rim that has three thread starts thereon, each of said thread starts having a respective start end and a finish end, said cap having a central body for closing off the opening at the neck of the bottle and an outer crown integral with the central body, said outer crown comprising an uninterrupted 32 teeth berit around and fixed onto the rim, wherein the number of teeth crimped on each of the thread starts is different for at least one of the thread starts with respect to the other two thread starts, thereby reducing the tendency of the cap to unscrew itself, whereby the number of teeth is different to a whole multiple of the number of thread starts such that at most only one tooth of said cap is ever located at and aligned with one of said thread start and finish ends, thereby reducing a propensity for said contents to leak from said bottle before said cap is removed therefrom.

\* \* \* \* \*